United States Patent [19]
Bell et al.

[11] Patent Number: 5,360,595
[45] Date of Patent: Nov. 1, 1994

[54] PREPARATION OF DIAGNOSTIC TEST STRIPS CONTAINING TETRAZOLIUM SALT INDICATORS

[75] Inventors: Douglas E. Bell; Amy H. Chu, both of Elkhart, Ind.

[73] Assignee: Miles Inc., Elkhart, Ind.

[21] Appl. No.: 108,295

[22] Filed: Aug. 19, 1993

[51] Int. Cl.$^5$ ............................................. G01N 21/00
[52] U.S. Cl. ........................................ 422/56; 422/58; 436/166
[58] Field of Search ............................. 422/56, 58, 61; 436/164, 166

[56] References Cited

U.S. PATENT DOCUMENTS 4,221,864  9/1980  Iytaka et al. .................... 430/572
5,063,153  11/1991  Arai et al. ....................... 422/56

Primary Examiner—Lyle A. Alexander
Attorney, Agent, or Firm—Jerome L. Jeffers

[57] ABSTRACT

Disclosed is an improved procedure for the manufacture of a diagnostic test device comprising a matrix having uniformly dispersed a tetrazolium salt and a reagent system designed to convert the tetrazolium to its colored formazan upon contacting the matrix with a fluid containing an analyte whose presence and/or concentration is being sought. The procedure involves applying the tetrazolium salt to the matrix from its solution in an organic solvent and, after drying, applying the reagent system to the matrix from its aqueous solution to which has been added hexanesulfonate as wetting agent.

17 Claims, 2 Drawing Sheets

PREPARATION OF DIAGNOSTIC TEST STRIPS CONTAINING TETRAZOLIUM SALT INDICATORS

BACKGROUND OF THE INVENTION

Tetrazolium salts, such as 2-(4-iodophenyl)-3-(4-nitrophenyl)-5-phenyl tetrazolium (INT), are useful in the measurement of analytes which can be converted to an equivalent concentration of NADH due to the reduction of the tetrazolium cation to its corresponding formazan which reduction can be accurately measured by colorimetric means.

A typical reagent system for determining concentration of an analyte, such as glucose, in body fluids is based on reductive chemistry wherein the primary components are hexokinase (HK), adenosine triphosphate (ATP), glucose-6-phosphate dehydrogenase (G-6-PDH), diaphorase, nicotinamideadenine dinucleotide (NAD) and a tetrazolium salt as indicator. In operation, hexokinase catalyzes the reaction in which, in the presence of the analyte, e.g. glucose, and magnesium as enzyme activator a phosphate radical is taken from ATP thereby converting it to adenosine diphosphate to form glucose-6-phosphate which is oxidized in the presence of NAD and G-6-PDH thereby reducing NAD to NADH. The NADH, in the presence of diaphorase as electron acceptor, reduces the colorless tetrazolium salt to its colored formazan counterpart thereby providing a detectable response which is directly quantitative for the detection of NADH and indirectly quantitative for the analyte whose presence triggers the reduction of NAD to NADH.

Tetrazolium salt indicators are commonly used with dry reagent formulations which employ diaphorase or a chemical mediator in the color generating step. An adequate amount of the indicator must be present to completely consume the reducing equivalents that originate from the influx of an analyte such as glucose into the reagent system.

U.S. Pat. No. 3,655,382 discloses tetrazolium thiazolium salts in which the counteranion can be chloride, iodide, bromide, thiocyanate, thiosulfate, sulfate, para-toluenesulfonate, methylsulfonate, ethyl sulfate, nitrate, acetate, perchlorate, perborate, sulfite, hydroxide or carbonate.

In U.S. Pat. No. 4,221,864 the patentees state that one of the objects of their invention is to provide a novel light sensitive photographic material containing a tetrazolium compound. They point out that this and other objects can be attained by preparing a photographic material which comprises a support and at least one light sensitive silver halide layer and another hydrophylic colloidal layer coated on the support, one of which layers contains a tetrazolium salt. They point out that where the salt of a tetrazolium compound is used as a non-diffusible ingredient, such salt can be synthesized by reacting a tetrazolium cation with an anion capable of making the selected compound non-diffusible. Counteranions such as those derived from higher alkylbenzenesulfonic acids, e.g. dodecylbenzenesulfonic acid or a higher alkyl sulfuric acid such as lauryl sulfate are disclosed.

Co-pending U.S. application Ser. No. 07/898,317 discloses sulfonate and phosphonate salts of tetrazolium compounds which exhibit unexpectedly high solubility in polar solvents. Also disclosed in this application is the manufacture of a test strip by first dipping a substrate in a methanol solution of the benzenesulfonate salt of tetrazolium indicator compounds and then contacting it with an aqueous solution of adenosine triphosphate.

SUMMARY OF THE INVENTION

The present invention involves a method for preparation of a diagnostic device comprising a matrix material as substrate having dispersed therein a tetrazolium salt as indicator and a reagent system which will convert the tetrazolium to its corresponding formazan when the device is brought into contact with a solution containing a predetermined analyte. The method involves the steps of:

a) contacting the matrix with a solution comprising the tetrazolium salt dissolved in an organic solvent and drying the matrix to thereby provide a matrix having the tetrazolium salt uniformly dispersed therein; and b) contacting the matrix having the tetrazolium salt uniformly dispersed therein with an aqueous solution of the reagent system which solution contains an alkylsulfonate of 5–7 straight chain carbon atoms and drying the matrix to thereby deposit the reagent system onto the matrix without eluting a significant amount of the tetrazolium salt therefrom and provide a matrix having the tetrazolium salt and reagent system uniformly dispersed therein.

DESCRIPTION OF THE INVENTION

Figure 1:
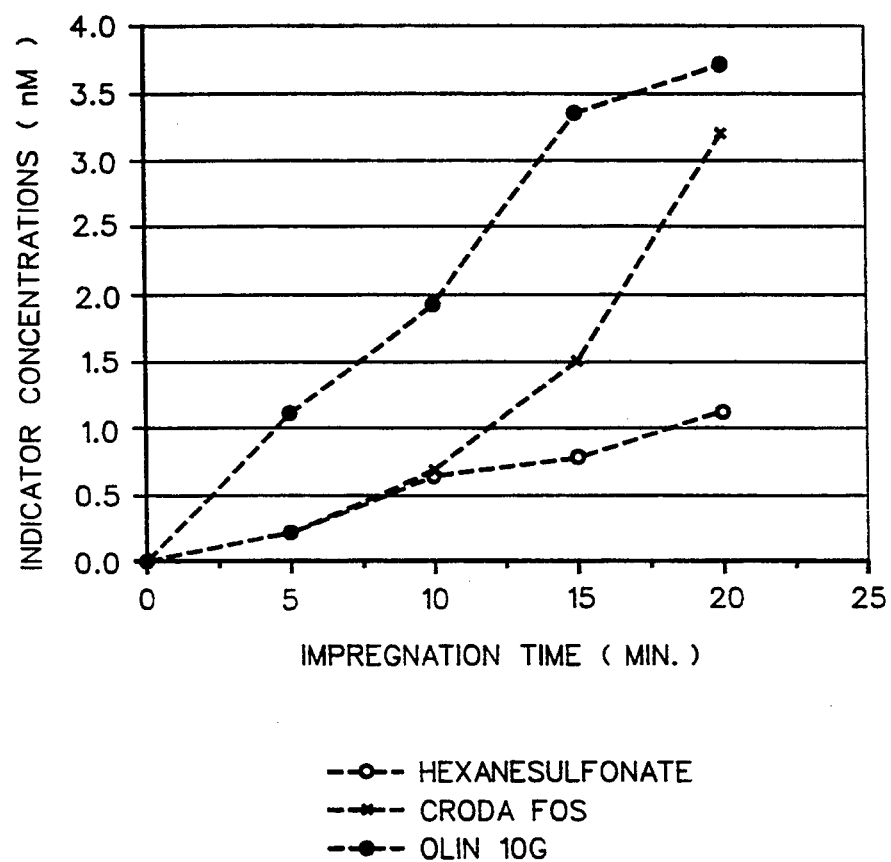
FIG. 1 graphically illustrates the effect of various surfactants on back extraction of indicator into the impregnation solution.

Tetrazolium salts suitable for use in the present invention are represented by the formula:

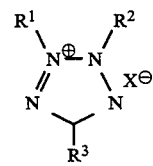

wherein $X^\ominus$ is a counteranion such as, for example, chloride, bromide, or iodide. Typically, $R^1$ and $R^3$ are phenyl groups and $R^2$ is phenyl or 2-thiazolyl. The phenyl groups and optional thiazolyl groups can be substituted or unsubstituted. More specifically, $R^1$, $R^3$ and optionally $R^2$ can be represented by, but are not limited to, the formula:

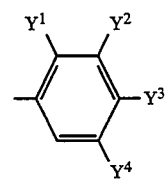

wherein the Y groups ($Y^1$, $Y^2$, $Y^3$, $Y^4$), which are the same or different, can be, for example, alkoxy, aryloxy, alkyl, amido, alkylamido, arylamido, alkylthio, arylthio, halo, hydrogen, hydroxy, carbamoyl, carbalkoxy, carboxyl, cyano, nitro, sulfo, sulfonamido, sulfamoyl, trialkylamino or ureido groups. Preferably, the alkyl groups each contain from 1 to 6 carbon atoms and the aryl groups are phenyl, naphthyl, pyridyl, oxazolyl, quinolyl, thiazolyl, thienyl and furanyl.

When $R^2$ is a thiazole group, it can be substituted or unsubstituted. For example, where the thiazole group is represented by the formula:

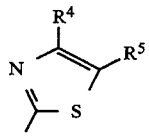

and $R^4$ and $R^5$ are hydrogen or some other substituent. In a preferred embodiment of the present invention, the $R^1$ and $R^3$ moieties of the tetrazolium salt are as described above and $R^2$ is a thiazole group in which $R^4$ and $R^5$ together form a benzo ring which is substituted or unsubstituted; $R^4$ is carboxyl, carbalkoxy, carbamoyl or cyano and $R^5$ is alkyl or chloro; $R^4$ is alkyl or aryl and $R^5$ is carboxyl, carbalkoxy, carbaryloxy, carbamoyl or cyano; $R^4$ is di- or trifluoroalkyl wherein the fluoro substituents are on the carbon adjacent to the thiazole residue; or one or both of $R^4$ and $R^5$ are substituted or unsubstituted phenyl, and if only one is substituted phenyl, the other is hydrogen or alkyl. Among those tetrazolium cations that are particularly useful in the context of the present invention are those in which $R^4$ and $R^5$ together form a benzo ring, which can be substituted or unsubstituted to give a benzthiazole residue having the formula:

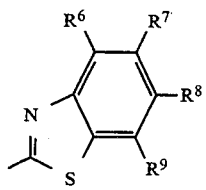

wherein
(i) $R^6$ and $R^7$ or $R^7$ and $R^8$ or $R^8$ and $R^9$ together form a benzo or cyclohexyl ring that is unsubstituted or substituted with alkoxy, aryloxy, alkyl, amido, alkylamido, arylamido, alkylthio, arylthio, amino, carbamoyl, carbalkoxy, cyano, halo, hydroxyl, sulfo, sulfonamido, sulfamoyl, trialkylamino or ureido and wherein the other substituents, which can be the same or different, are hydrogen, alkoxy, aryloxy, alkyl, amido, alkylamido, arylamido, alkylthio, arylthio, amino, carbamoyl, carbalkoxy, cyano, halo, hydroxyl, sulfo, sulfonamido, sulfamoyl, trialkylammonio or ureido provided that when $R^7$ and $R^8$ together for a benzo or cyclohexyl ring, $R^6$ is not hydrogen, or
(ii) one or more of $R^6$, $R^7$, $R^8$ and $R^9$ is alkoxy, aryloxy, alkyl, amido, alkylamido, arylamido, alkylthio, arylthio, amino, carbamoyl, carbalkoxy, cyano, halo, hydroxyl, sulfo, sulfonamido, sulfamoyl, trialkylammonio or ureido, and the others, if any, are hydrogen.

Suitable matrix materials for use in the present invention are known in the art and include adsorbent papers, woven and nonwoven cloth, glass fiber filters, polymeric membranes and films. A preferred matrix material comprises a zwitterionic charged nylon fabric with a pore size ranging from to 0.45 to 0.8μ. Absorbant or swellable carriers such as filter paper, absorbant glass fiber filters or synthetic nonwovens are impregnated or sprayed with the tetrazolium salt/organic solvent solution and then dried whereupon the matrix is treated with an aqueous solution of the reagent system and dried again to provide a diagnostic test device, which, when contacted with a solution containing an appropriate analyte, will provide a detectable response due to the conversion of the tetrazolium salt to its corresponding, colored formazan.

The tetrazolium salts are typically only marginally soluble in water thereby necessitating the use of organic solutions for their deposition onto the matrix material. Suitable organic solvents include, for example, methanol and acetone. Typically, tetrazolium salt solutions ranging from 50 to 100 mM, preferably, 70 to 90 mM, in concentration are used for deposition of the tetrazolium salt onto the matrix material substrate.

The reagent system will typically comprise one or more enzymes such as hexokinase (HK) and glucose-6-phosphate dehydrogenase, a co-factor such as adenosine triphosphate (ATP), magnesium, an oxidizing agent such as nicotinamide-adenine dinucleotide and an electron acceptor such as diaphorase. In operation, hexokinase catalyzes the reaction in which a phosphate radical is taken from ATP to form glucose-6-phosphate which is oxidized in the presence of NAD and glucose-6-phosphate dehydrogenase thereby reducing the NAD to NADH. The NAD, in the presence of diaphorase as electron acceptor, reduces the colorless tetrazolium salt to an intensely colored formazan salt. The reaction steps, which are set out in the following scheme, represent the determination of NADH as an indirect means of determining the glucose concentration of the test sample:

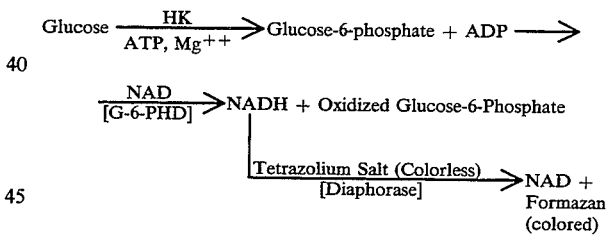

Alternative enzymes for inclusion in the reagent system include glucose dehydrogenase. When the presence or concentration of an analyte other than glucose, such as cholesterol or triglyceride, is being sought, an enzyme selective for the particular analyte or its reaction products would be employed.

The reagent system is applied to the matrix from its aqueous solution. In a typical run for the preparation of a device for the detection of glucose the solution will contain:

| Reagent | Concentration | Preferred Concentration |
|---|---|---|
| Hexokinase | 1500 to 3500 IU/mL | 2000 to 3000 IU/mL |
| Adenosine Triphosphate | 50 to 120 mM | 70 to 110 mM |
| Magnesium | 30 to 70 mM | 40 to 60 mM |
| Glucose-6-Phosphate Dehydrogenase | 600 to 1600 IU/mL | 900 to 1320 IU/mL |
| Diaphorase | 500 to 1200 mM | 650 to 1000 mM |

In addition, the reagent system can contain polymers such as polyvinyl alcohol and/or carboxymethylcellulose as color stabilizers, a buffer such as HEPES, bovine serum albumin as enzyme stabilizer and oxamic acid to inhibit any extraneous lactate dehydrogenase. In addition, a surfactant is required to facilitate the application of the reagent system to the matrix. Ideally, the surfactant should exhibit the following characteristics:
1. Cause rapid wetting of the reagent system into the matrix by reducing the surface tension of the matrix containing the dried tetrazolium.
2. Maintain the wetting property of the membrane after thermal stress, i.e. maintain the reagent system wettability upon rehydration through the shelf life of the diagnostic device.
3. Not cause extraction of the indicator into the aqueous impregnation solution.

Of the various surfactants tried, only alkanesulfonates of 5-7 carbon atoms were found to possess all these properties. Hexane sulfonate is particularly useful in this regard. It has been discovered that using these alkanesulfonates as the surfactant in the reagent system formulation prevents leaching of dried indicator back into the aqueous phase possibly due to the size and hydrophilicity of these surfactants. This was not achieved with other surfactants such as Croda FOS (phosphated cetyl ether), Olin 10G (para-nonylphenoxypolyglycidol), Surfynol (tetramethyldecynediol ethoxylated with 30 moles of ethylene oxide), Triton (octyl phenoxy polyethoxy ethanol), Silwet (polyalkyleneoxide modified dimethylsiloxanes), short chain alkanesulfonates such as methanesulfonate or propanesulfonate or longer chain alkanesulfonates such as those containing from 8-10 carbon atoms. Hexanesulfonate also enhances the wetting characteristics of the reagent system. Problems caused by back extraction of the tetrazolium indicator, poor wetting of the reagent system and lot-to-lot variability are also minimized.

Hexanesulfonate, represented by the formula:

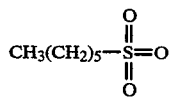

is commercially available. In the practice of the present invention it is typically added to the aqueous reagent system solution in an amount of from 0.5% to 1.3% w/v and preferably from 0.7% to 1.1% w/v. By impregnating the matrix with the tetrazolium salt first and removing the organic solvent by evaporation with subsequent application of the reagent system comprising other essential ingredients for the color forming reaction from its aqueous solution containing the hexanesulfonate wetting agent, the back extraction of the tetrazolium indicator into the aqueous solution is substantially prevented while ensuring the rewettability of the reagent system upon rehydration of the matrix.

The present invention is further illustrated by the following examples:

EXAMPLE I

The tetrazolium indicator, 2-(4-iodophenyl)-3-(4-nitrophenyl)-5-phenyltetrazolium chloride (INT) or 2,2',5,5'-tetraphenyl-3,3'(3,,3'-dimethoxy-4,4'-diphenylene) ditetrazolium chloride (NBT), was dissolved in a solution of methanol or 50 parts methanol/50 parts dimethyl formamide to a concentration of 80 mM. The solution was immersion impregnated onto a solid support of paper or membrane (e.g. Pall Biodyne A membrane) and dried in an oven at 50° C. for approximately 10 minutes. The dried indicator matrix was then impregnated with an aqueous solution containing enzymes, substrates and surfactant (hexane sulfonate and other surfactants for comparison) whereupon the impregnated support was dried again. The concentrations of the reagents in the impregnation mixtures are listed below:

Run #1 (Glucose reagent using Hexokinase)
  5.5% (w/w) Tetrazolium indicator
  4% (w/w) HEPES buffer at pH 7.5
  2% (w/w) NAD
  6% (w/w) ATP
  1% (w/w) surfactant
  1% (w/w) Mg++
  2500 Units/mL Hexokinase
  1000 Units/mL Glucose-6-phosphate Dehydrogenase
  800 Units/mL Diaphorase
  3% (w/w) Inactive ingredients Run #2 (Glucose reagent using Glucose Dehydrogenase)
  3.5% (w/w) Tetrazolium indicator
  4% (w/w) HEPES buffer at pH 7.5
  2% (w/w) NAD
  1% (w/w) surfactant
  2000 Units/mL Glucose Dehydrogenase
  800 Units/mL Diaphorase
  3% Inactive ingredients Run #3 (Cholesterol reagent)
  1.5% Tetramethylbenzidine hydrochloride indicator
  4% Pipes buffer at pH 7.0
  240 Units/mL Peroxidase
  240 Units/mL Cholesterol Esterase
  120 Units/mL Cholesterol Oxidase
  1% Surfactant
  3% Inactive ingredients Run #4 (Triglyceride reagent)
  1.1% Tetrazolium indicator
  2.4% HEPES buffer at pH 7.5
  0.7% Mg++
  2.7% ATP
  7.1% NAD
  25,000 Units/mL Lipase
  800 Units/mL Glycerol Kinase
  1,000 Units/mL Glycerol-3-Phosphate Dehydrogenase
  500 Units/ml Diaphorase
  1% Surfactant
  1.5% Inactive ingredients To determine the amount of indicator extracted back into the second impregnation solution (i.e. the aqueous medium), the solution was sampled every 5 minutes during impregnation and the concentration of indicator in the solution was determined by HPLC.

To simulate reagent performance at the end of shelf-life, accelerated stress of the reagent system at an elevated temperature (typically 60° C.) is employed. Surfactants are often added into dry reagent formulations to ensure fast reconstitution of the dry reagents especially when the reagent has reached the end of its shelf life. Typically, a reagent without a surfactant shows a decreased dose response and poor precision after thermal stress resulting from poor wetting upon rehydration. For a reagent with a surfactant, such as hexane sulfonate, there is no change in reagent performance after thermal stress. However, not all surfactants perform as well in this regard as hexanesulfonate. The effect of various surfactants on the reagent performance, using the formulation of run #1, is set out in Table I.

TABLE I

Effect of Surfactant on Reagent Dose Response

| Surfactant | Dose Response Slope* | |
|---|---|---|
| | Room Temp. | Stressed at 60° C. for 5 Days |
| None | 0.71 | 0.165 |
| Hexanesulfonate | 1.037 | 1.059 |
| Pentanesulfonate | 0.996 | 1.017 |
| Croda FOS | 1.003 | 1.002 |
| Olin 10G | 0.975 | 1.017 |
| Benzene Sulfonate | 1.063 | 0.85 |
| Surfynol | 1.126 | 0.785 |
| Silwet | 0.8 | 0.538 |
| Triton | 1.15 | 0.71 |

*Reagent reactivity plotted against plasma glucose (mg/dL).

EXAMPLE II

Reagents made with hexanesulfonate, pentane sulfonate, Croda FOS or Olin 10G show no significant change in reagent dose response after stress. However, reagents made with benzene sulfonate, Triton, Silwet or Surfynol showed significantly decreased reactivity after thermal stress. Surfactants demonstrating suitable reagent reactivity retention, Croda FOS or Olin 10G, are not suitable for use with tetrazolium indicators because of the severe backextraction encountered with the use of these surfactants. Compared with hexanesulfonate, tetrazolium indicator back extraction caused by Croda FOS or Olin 10G is 3 to 4 times more severe than that encountered using hexanesulfonate during the reagent impregnation step. This is illustrated by FIG. 1. To determine which surfactant (Hexanesulfonate, Croda FOS or Olin 10G) used in the second impregnation solution causes the worst indicator back extraction) three impregnation solutions were made as described above with each containing 1% of the particular surfactant and used to impregnate a nylon substrate, i.e. Pall Biodyne A, that had previously been impregnated with 2-(4-difluoromethyl-5-chlorothiazol-2-yl)-3-(3,4,5-trimethoxyphenyl)-5-(3,4-methylenedioxyphenyl) tetrazolium salt. Samples of the $2^{nd}$ application solutions were taken at 0, 5, 10 and 20 minutes after commencement of the $2^{nd}$ impregnation and the concentration of the tetrazolium indicator determined using HPLC. The data shown in FIG. 1 represent the amount of indicator back-extracted into the $2^{nd}$ impregnation solution during the second impregnation procedure.

EXAMPLE III

Reagents were made with 1% of various organosulfonates (methane, propane, pentane, hexane, heptane, octane, decane and benzene) in the second impregnation solution and applied to the nylon substrate containing the tetrazolium indicator from the first impregnation. The majority of the $2^{nd}$ impregnation solutions remained clear after addition of the organo sulfonate, except for those exposed to methane-, octane and decane sulfonate which became cloudy due to enzyme precipitation by the organosulfonate. The dose responses of the dried reagents were determined with glycolyzed 40% hematocrit whole blood which had been spiked to 50, 100, 250, 450 and 600 mg/dL plasma glucose. Twenty replicates per sample were run on 5 commercially available reflectance type glucose meters with the endpoint reflectance being used to calculate reagent reactivity. The performance of the reagent with various organosulfonates was evaluated with 40% hematocrit whole blood samples. The results indicate that reagent containing pentanesulfonate, hexanesulfonate or heptanesulfonate shows high reactivity (FIG. 2) and good stability after heat stress (Table 1). Alkanesulfonates with either shorter chain (less than C5, such as methanesulfonate and propanesulfonate) or longer chain (greater than C7, such as octanesulfonate and decanesulfonate) can either cause enzyme precipitation during impregnation resulting in low reactivity or make the finished product less resistant to heat stress.

Figure 2:
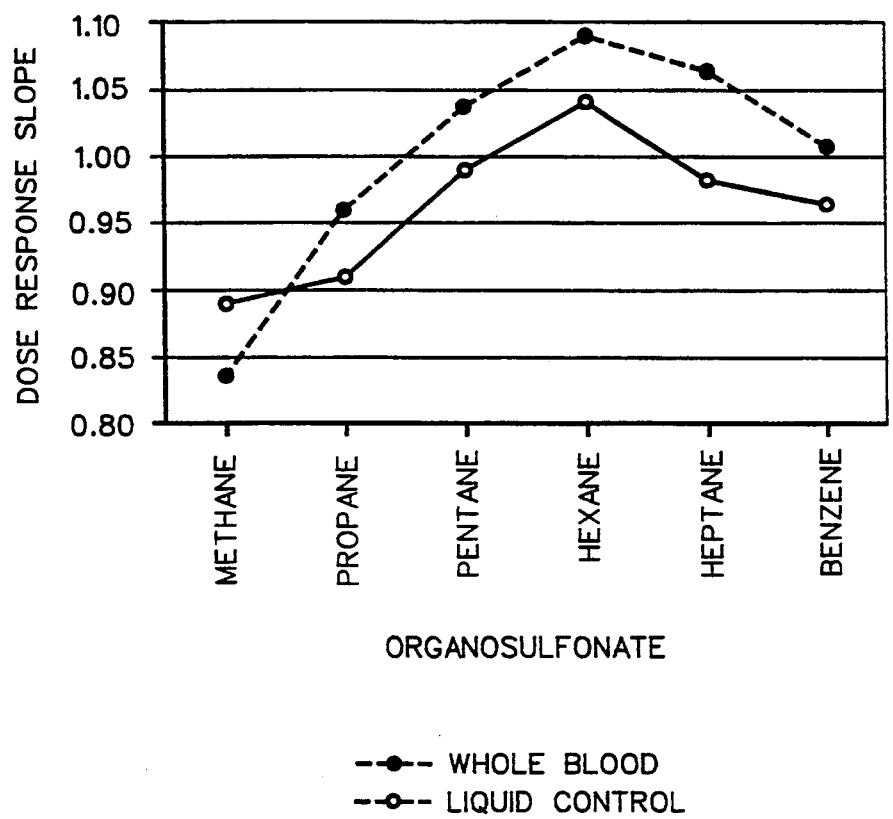
FIG. 2 represents the effect of the organo sulfonate on the reagents reactivity.

The reagents were also tested with glucose liquid control samples to prove that the results shown in FIG. 2 were not due to interactions between red blood cells and reagent chemistry. These tests provided results similar to those observed with the blood samples.

What is claimed is:

1. In the method of applying an indicator/reagent system to a matrix carrier, said indicator comprising a tetrazolium salt which, in the presence of the reagent system and a predetermined analyte will undergo a redox reaction resulting in its reduction to a colored formazan, the improvement which comprises:
   a) contacting the matrix with a solution comprising the tetrazolium salt in an organic solvent and drying the matrix to thereby provide a matrix having the tetrazolium salt uniformly dispersed therein; and
   b) contacting the matrix having the tetrazolium salt uniformly dispersed therein with an aqueous solution of the reagent system which solution contains an alkylsulfonate of 5-7 straight chain carbon atoms and drying the matrix to thereby deposit the reagent system onto the matrix without eluting a significant amount of the tetrazolium salt therefrom and provide a matrix having the tetrazolium salt and reagent system uniformly dispersed therein.

2. The method of claim 1 wherein the reagent system contains hexokinase, adenosine triphosphate, glucose-6-phosphate dehydrogenase, diaphorase and nicotinamideadenine dinucleotide.

3. The method of claim 1 wherein the tetrazolium salt is represented by the formula:

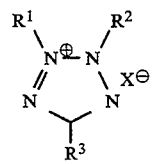

wherein $X^{\ominus}$ is a counteranion, $R^1$ and $R^3$ are substituted or unsubstituted phenyl groups and $R^3$ is substituted or unsubstituted phenyl or 2-thiazolyl.

4. The method of claim 1 wherein the matrix material is an absorbant paper, a woven or nonwoven cloth, a glass fiber filter, or a polymeric membrane or film.

5. The method of claim 4 wherein the matrix material is a porous zwitterionic charged nylon fabric having pore sizes ranging from 0.45 to 0.8μ.

6. The method of claim 1 wherein the alkyl sulfonate is present in the solution in a concentration of from 0.5% to 1.3% w/v.

7. The method of claim 6 wherein the alkanesulfonate is present in an amount of from 0.7% to 1.1% w/v.

8. A method of applying an indicator/reagent system to a matrix carrier of a porous zwitterionic charged nylon fabric, said indicator comprising a tetrazolium salt capable of undergoing a redox reaction resulting in its reduction to a colored formazan in the presence of the reagent system and a predetermined analyte which method comprises:
   a) contacting the matrix with a solution comprising the tetrazolium salt in an organic solvent and drying the matrix to thereby provide a matrix having the tetrazolium salt dispersed therein; and
   b) contacting the matrix having the tetrazolium salt dispersed therein with an aqueous solution of the reagent system comprising hexokinase, adenosine triphosphate, glucose-6-phosphate dehydrogenase, diaphorase and nicotinamideadenine dinucloetide which solution contains an alkylsulfonate of 5-7 straight chain carbon atoms and drying the matrix to thereby deposit the reagent system onto the matrix while reducing the amount of tetrazolium salt which is eluted from the matrix from the aqueous solution.

9. The method of claim 8 wherein the alkanesulfonate is hexane sulfonate and is present in the aqueous solution in a concentration of from 0.5% to 1.3% w/v.

10. The method of claim 9 wherein the hexane sulfonate is present in the aqueous solution in a concentration of from 0.7% to 1.1% w/v.

11. A diagnostic test device prepared by:
   a) contacting a matrix carrier with a solution comprising a tetrazolium salt which, in the presence of a reagent system and a predetermined analyte will undergo a redox reaction resulting in its reduction to a colored formazan in an organic solvent and drying the matrix to thereby provide a matrix having the tetrazolium salt uniformly dispersed therein; and
   b) contacting the matrix having the tetrazolium salt uniformly dispersed therein with an aqueous solution of the reagent system which solution contains an alkylsulfonate of 5-7 straight chain carbon atoms and drying the matrix to thereby deposit the reagent system onto the matrix to provide a matrix having the tetrazolium salt and reagent system uniformly dispersed therein.

12. The device of claim 11 wherein the reagent system contains hexokinase, adenosine triphosphate, glucose-6-phosphate dehydrogenase, diaphorase and nicotinamideadenine dinucleotide.

13. The device of claim 11 wherein the tetrazolium salt is represented by the formula:

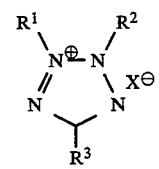

wherein $X^{\ominus}$ is a counteranion, $R^1$ and $R^3$ are substituted or unsubstituted phenyl groups and $R^3$ is substituted or unsubstituted phenyl or 2-thiazolyl.

14. The device of claim 11 wherein the matrix material is an absorbent paper, a woven or nonwoven cloth, a glass fiber filter, or a polymeric membrane or film.

15. The device of claim 11 wherein the matrix material is a porous zwitterionic charged nylon fabric having pore sizes ranging from 0.45 to 0.8μ.

16. The device of claim 11 wherein the alkyl sulfonate is present in the solution in a concentration of from 0.5% to 1.3% w/v.

17. The device of claim 11 wherein the alkanesulfonate is present in an amount of from 0.7% to 1.1% w/v.

* * * * *